(12) United States Patent
Gardel et al.

(10) Patent No.: US 7,776,348 B2
(45) Date of Patent: Aug. 17, 2010

(54) WATER-IN-OIL EMULSION FOUNDATION

(75) Inventors: Nadia Gardel, Bourg la Reine (FR); Véronique Barrois, Paris (FR)

(73) Assignee: L'Oreal S.A., Paris (FR)

( * ) Notice: Subject to any disclaimer, the term of this patent is extended or adjusted under 35 U.S.C. 154(b) by 1033 days.

(21) Appl. No.: 10/603,698

(22) Filed: Jun. 26, 2003

(65) Prior Publication Data

US 2005/0008592 A1 Jan. 13, 2005

Related U.S. Application Data

(60) Provisional application No. 60/401,028, filed on Aug. 6, 2002.

(30) Foreign Application Priority Data

| Jun. 26, 2002 | (FR) | 02 07937 |
|---|---|---|
| Oct. 2, 2002 | (FR) | 02 12190 |

(51) Int. Cl.
*A61Q 1/02* (2006.01)
*A61Q 19/04* (2006.01)
*A61Q 1/00* (2006.01)
*A61Q 1/12* (2006.01)
*A61K 8/00* (2006.01)
*A61K 8/18* (2006.01)
*A61K 31/74* (2006.01)
*A61K 8/02* (2006.01)

(52) U.S. Cl. ............... 424/401; 424/63; 424/69; 424/78.03; 514/844; 514/845

(58) Field of Classification Search ........... 424/401, 424/63, 69, 78.03; 514/844, 845
See application file for complete search history.

(56) References Cited

U.S. PATENT DOCUMENTS

| 4,552,753 | A | * | 11/1985 | Elm et al. .................. 424/66 |
|---|---|---|---|---|
| 5,843,417 | A | * | 12/1998 | Hanna et al. .............. 424/70.7 |
| 5,851,539 | A | | 12/1998 | Mellul et al. |
| 5,919,468 | A | * | 7/1999 | Bara ..................... 424/401 |
| 6,159,486 | A | | 12/2000 | Terren et al. |
| 6,221,343 | B1 | | 4/2001 | Richard et al. |
| 6,224,851 | B1 | * | 5/2001 | Bara ..................... 424/59 |
| 6,338,839 | B1 | | 1/2002 | Auguste et al. |
| 6,342,469 | B1 | | 1/2002 | Lorant |
| 6,344,204 | B1 | | 2/2002 | Lorant |
| 6,383,503 | B1 | | 5/2002 | Bleckmann et al. |
| 6,426,079 | B1 | | 7/2002 | Bara et al. |
| 6,440,430 | B1 | | 8/2002 | Bara et al. |

FOREIGN PATENT DOCUMENTS

| EP | 0 595 683 | 5/1994 |
|---|---|---|
| EP | 0 856 307 A2 | 8/1998 |
| EP | 0 856 309 | 8/1998 |
| EP | 0 950 401 | 10/1999 |
| EP | 0 979 646 | 2/2000 |
| EP | 1 028 120 | 8/2000 |
| EP | 1 034 774 | 9/2000 |
| EP | 1 055 423 | 11/2000 |
| EP | 1 086 683 | 3/2001 |
| FR | 2 776 513 | 10/1999 |
| FR | 2 776 514 | 10/1999 |
| FR | 2 776 515 | 10/1999 |
| FR | 2 786 697 A1 | 6/2000 |
| FR | 2 789 313 | 8/2000 |
| JP | 11-5714 | 1/1990 |
| JP | 11-246330 | 9/1999 |
| JP | 2000-072645 | 3/2000 |
| JP | 2000-169335 | 6/2000 |
| WO | WO 96/14076 | 5/1996 |
| WO | WO 99/30681 | 6/1999 |
| WO | WO 99/47111 | 9/1999 |
| WO | WO 00/72817 | 12/2000 |
| WO | WO 01/00141 | 1/2001 |

OTHER PUBLICATIONS

Aldrich Catalog 2003-2004.*
English language Derwent Abstract of EP 1 086 683, Mar. 28, 2001.
English language Derwent Abstract of FR 2 776 513, Oct. 1, 1999.

(Continued)

*Primary Examiner*—Shengjun Wang
*Assistant Examiner*—Kara R McMillian
(74) *Attorney, Agent, or Firm*—Finnegan, Henderson, Farabow, Garrett & Dunner, LLP

(57) ABSTRACT

A foundation in the form of a water-in-oil emulsion comprising a fatty phase, an aqueous phase, at least one surfactant chosen from $C_8$-$C_{22}$ alkyl dimethicone copolyols, at least one other surfactant chosen from dimethicone copolyols, and hydrophobic coated pigments, where the fatty phase comprises at least 30% by weight, relative to the total weight of the emulsion, of a volatile fatty phase comprising:
  at least 6% by weight, relative to the total weight of the emulsion, of at least one volatile hydrocarbon oil, and
  at least one volatile oil chosen from silicone volatile oils and fluorinated volatile oils; wherein the foundation is stable after storing at room temperature (25° C.) for at least 2 months and makes it possible to obtain a homogeneous make-up on the skin.

83 Claims, No Drawings

OTHER PUBLICATIONS

"Microemulsions Theory and Practice", L.M. Prince Ed., Academic Press (1977), pp. 21-32.
English language Derwent abstract for FR 2 786 697 A1.
English language Derwent abstract for JP 11-246330.
English language Derwent abstract for JP 2000-072645.
English language Derwent abstract for JP 2000-169335.
Fragrance Journal, Nov. 2000, pp. 17 to 22, Fragrance Journal Ltd.

* cited by examiner

WATER-IN-OIL EMULSION FOUNDATION

This application claims benefit of U.S. Provisional Application No. 60/401,028, filed Aug. 6, 2002.

Disclosed herein is a foundation cosmetic composition in the form of a water-in-oil emulsion comprising silicone surfactants and a volatile oil. Further disclosed herein is a method for applying make-up to the skin comprising applying the foundation to the skin.

The foundation composition is a make-up composition for the skin of human beings. The composition disclosed herein may, for example, be provided in at least one of the following forms: a foundation to be applied to the face or the neck; a concealer; a tinted cream; and a make-up composition for the body.

Foundation compositions are commonly used to give an aesthetic color to the skin, for example, to the face, but also can be used to conceal skin imperfections such as redness and spots.

FR-A-2686510 discloses water-in-oil foundation emulsions comprising, as a surfactant, an alkyl dimethicone copolyol, for example, a cetyl dimethicone copolyol. However, it has been observed that when these emulsions contain a large quantity (more than 15% by weight) of volatile oils, such as for example cyclopentasiloxane, the fluid emulsion may not be stable over time: the emulsion, after storing for 2 months, or even 4 months, at room temperature (25° C.), can release oil at the surface of the composition and therefore may no longer be homogeneous. The user must then thoroughly stir the composition before its use. If the composition is not stirred or is poorly stirred, the application of this composition to the skin may leave an uncomfortable sensation of greasiness and the make-up obtained may not be homogeneous, and marks of color may be visible on the skin.

The aim of the present inventors is to make available a foundation composition which can have good stability after storing at room temperature (25° C.) for at least 2 months, or even 4 months, and which may make it possible to obtain a homogeneous make-up on the skin.

The inventors have discovered that such a foundation could be obtained using at least one surfactant chosen from alkyl dimethicone copolyols, at least one other surfactant chosen from dimethicone copolyols and a mixture of volatile oils in a large amount.

For example, disclosed herein is a foundation in the form of a water-in-oil emulsion comprising a fatty phase; an aqueous phase; at least one surfactant chosen from $C_8$-$C_{22}$ alkyl dimethicone copolyols; at least one other surfactant chosen from dimethicone copolyols; and hydrophobic coated pigments; wherein the fatty phase comprises at least 30% by weight, relative to the total weight of the emulsion, of a volatile fatty phase comprising:
   at least 6% by weight, relative to the total weight of the emulsion, of at least one volatile hydrocarbon oil, and
   at least one volatile oil chosen from volatile silicone oils and volatile fluorinated oils.

Further disclosed herein is a cosmetic method for the non-therapeutic application of make-up to the skin which comprises applying to the skin the composition as defined above.

Also disclosed herein is the use of a composition as defined above for obtaining a homogeneous make-up on the skin.

Even further disclosed herein is the use of at least one surfactant chosen from $C_8$-$C_{22}$ alkyl dimethicone copolyols and of at least one other surfactant chosen from dimethicone copolyols in a foundation composition in the form of a water-in-oil emulsion comprising a fatty phase; an aqueous phase; and hydrophobic coated pigments, wherein the fatty phase comprises at least 30% by weight, relative to the total weight of the emulsion, of a volatile fatty phase comprising:
   at least 6% by weight, relative to the total weight of the emulsion, of at least one volatile hydrocarbon oil, and
   at least one volatile oil chosen from volatile silicone oils and volatile fluorinated oils, wherein the composition has at least one property of being stable, homogeneous, and capable of obtaining a homogeneous make-up on the skin.

The emulsion disclosed herein may have very good stability at room temperature (25° C.), for example, after storage for 2 months, and further, for example, for 4 months. The foundation can also have at least one quality of being easily applied to the skin, with a sensation of unctuousness, softness and non-greasiness, spreading homogeneously on the skin, and drying rapidly after application. The make-up obtained can be homogeneous, without leaving any mark on the skin, and may exhibit good stability of the mattness over time.

The at least one surfactant chosen from $C_8$-$C_{22}$ alkyl dimethicone copolyols present in the foundation disclosed herein may, for example, be chosen from oxypropylenated and oxyethylenated polymethyl ($C_8$-$C_{22}$)alkyl dimethyl methyl siloxanes.

The $C_8$-$C_{22}$ alkyl dimethicone copolyols may, for example, be chosen from compounds of the following formula (I):

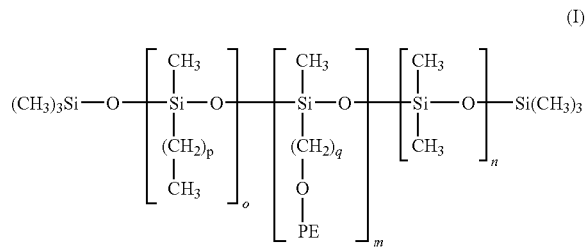

wherein:
PE is chosen from groups $(-C_2H_4O)_x-(C_3H_6O)_y-R$, wherein
   R is chosen from a hydrogen atom and alkyl radicals comprising from 1 to 4 carbon atoms,
   x is an integer ranging from 0 to 100, and
   y is an integer ranging from 0 to 80, provided that x and y are not simultaneously equal to 0;
m is an integer ranging from 1 to 40;
n is an integer ranging from 10 to 200;
o is an integer ranging from 1 to 100;
p is an integer ranging from 7 to 21; and
q is an integer ranging from 0 to 4.

and, for example:
R is a hydrogen atom;
m is an integer ranging from 1 to 10;
n is an integer ranging from 10 to 100;
o is an integer ranging from 1 to 30;
p is 15; and
q is 3.

For example, the $C_8$-$C_{22}$ alkyl dimethicone copolyols may be chosen from cetyl dimethicone copolyols such as the product marketed under the name Abil EM-90 by the company Goldschmidt.

The at least one surfactant chosen from $C_8$-$C_{22}$ alkyl dimethicone copolyols may be present, for example, in the emulsion disclosed herein in an amount ranging from 0.5% to 2% by weight, relative to the total weight of the emulsion, and further, for example, ranging from 0.6% to 2% by weight, relative to the total weight of the emulsion and, even further, for example, ranging from 0.7% to 2% by weight, relative to the total weight of the emulsion, and even further, for example, ranging from 0.8% to 2% by weight, relative to the total weight of the emulsion. Still further, the amount may range from 0.5% to 1.5% by weight, relative to the total weight of the emulsion, such as from 0.6% to 1.5% by weight, relative to the total weight of the emulsion, even further, for example, ranging from 0.7% to 1.5% by weight, relative to the total weight of the emulsion, and even further, for example, ranging from 0.8% to 1.5% by weight, relative to the total weight of the emulsion.

The dimethicone copolyols present in the foundation disclosed herein may, for example, be chosen from oxypropylenated and oxyethylenated polydimethyl-methylsiloxanes.

The dimethicone copolyols may, for example, be chosen from compounds corresponding to the following formula (II):

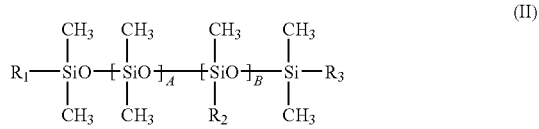

wherein:
  $R_1$, $R_2$, $R_3$, which may be identical or different, are each chosen from $C_1$-$C_6$ alkyl radicals and radicals —$(CH_2)_x$—$(OCH_2CH_2)_y$—$(OCH_2CH_2CH_2)_z$—$OR_4$, provided that at least one radical $R_1$, $R_2$ or $R_3$ is not an alkyl radical;
  $R_4$ is chosen from hydrogen, $C_1$-$C_3$ alkyl radicals and $C_2$-$C_4$ acyl radicals;
  A is an integer ranging from 0 to 200;
  B is an integer ranging from 0 to 50; provided that A and B are not simultaneously equal to zero;
  x is an integer ranging from 1 to 6;
  y is an integer ranging from 1 to 30; and
  z is an integer ranging from 0 to 5.

For example, in one embodiment, in the compound of formula (II), $R_1$=$R_3$=a methyl radical, x is an integer ranging from 2 to 6 and y is an integer ranging from 4 to 30. $R_4$ may, for example, be a hydrogen.

The compounds of formula (II) may, for example, be chosen from compounds of formula (III):

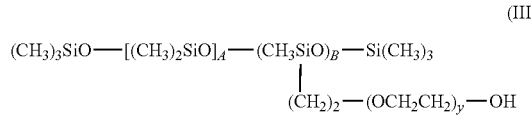

wherein:
  A is an integer ranging from 20 to 105;
  B is an integer ranging from 2 to 10; and
  y is an integer ranging from 10 to 20.

The compounds of formula (II) may, for example, also be chosen from compounds of formula (IV):

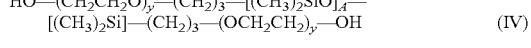

wherein: A' and y, which may be identical or different, are each an integer ranging from 10 to 20.

The dimethicone copolyols may, for example, be chosen from those compounds sold under the names DC 5329, DC 7439-146, DC2-5695, Q4-3667 by the company Dow Corning; and KF-6013, KF-6015, KF-6016, KF-6017 by the company Shin-Etsu.

The compounds DC 5329, DC 7439-146, DC2-5695 are compounds of formula (III) wherein respectively A is 22, B is 2 and y is 12; A is 103, B is 10 and y is 12; A is 27, B is 3 and y is 12.

The at least one other surfactant chosen from dimethicone copolyols may be present in the emulsion disclosed herein in an amount ranging, for example, from 5% to 10% by weight, relative to the total weight of the emulsion, and further, for example, ranging from 5% to 8% by weight, relative to the total weight of the emulsion and even further, for example, ranging from 5% to 7% by weight, relative to the total weight of the emulsion.

The hydrophobic coated pigments present in the emulsion disclosed herein are pigments which can be surface-treated with at least one hydrophobic agent in order to make them compatible with the fatty phase of the emulsion, for example, for them to have good wettability with the oils of the fatty phase. Thus, these treated pigments may be well dispersed in the fatty phase.

The pigments intended to be coated may be chosen from at least one of inorganic and organic pigments. The pigments may, for example, be chosen from at least one of metal oxides such as iron oxides, for example, iron oxides that are yellow, red, brown and black in color, titanium dioxides, cerium oxide, zirconium oxide, and chromium oxide; manganese violet, ultramarine blue, Prussian blue, ferric blue, bismuth oxychloride, pearl, mica coated with titanium, mica coated with bismuth oxychloride, colored pearlescent pigments such as mica-titanium with iron oxides, mica-titanium with, for example, ferric blue and chromium oxide, mica-titanium with an organic pigment of the abovementioned type and pearlescent pigments based on bismuth oxychlorides.

For example, pigments chosen from iron oxides and titanium dioxide may be used in the compositions disclosed herein.

The at least one hydrophobic treatment agent may be chosen, for example, from silicones such as methicones, dimethicones, perfluoroalkylsilanes; fatty acids such as stearic acid; metal soaps such as aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising at least one perfluoroalkyl perfluoropolyether group, amino acids; N-acylated amino acids and salts thereof; lecithin, and isopropyl triisostearyl titanate.

The N-acylated amino acids may comprise, for example, at least one acyl group comprising from 8 to 22 carbon atoms, such as 2-ethylhexanoyl, caproyl, lauroyl, myristoyl, palmitoyl, stearoyl and cocoyl groups. The salts of these compounds may, for example, be chosen from aluminium, magnesium, calcium, zirconium, zinc, sodium and potassium salts. The amino acids may, for example, be chosen from lysine, glutamic acid and alanine.

The term alkyl mentioned in the compounds cited above means an alkyl group comprising from 1 to 30 carbon atoms, for example, comprising from 5 to 16 carbon atoms.

Hydrophobic treated pigments are, for example, described in Patent Application No. EP-A-1086683.

The hydrophobic coated pigments may be present in an amount ranging, for example, from 0.5% to 20% by weight, relative to the total weight of the emulsion, for example, in an amount ranging from 5% to 20% by weight, relative to the total weight of the emulsion, even further, for example, ranging from 8% to 20% by weight, relative to the total weight of the emulsion, and further, for example, ranging from 8 to 15% by weight, relative to the total weight of the emulsion.

The fatty phase of the composition disclosed herein may comprise, for example, at least 30% by weight, relative to the total weight of the emulsion, of the volatile fatty phase comprising a mixture of volatile oils as defined above, for example, from 30% to 45% by weight, relative to the total weight of the emulsion, further, for example, from 30% to 40% by weight, relative to the total weight of the emulsion, and further, for example, from 33% to 38% by weight, relative to the total weight of the emulsion. For example, the mixture of volatile oils as defined above may be present in an amount ranging, for example, from 30% to 45% by weight, relative to the total weight of the emulsion, for example, from 30% to 40% by weight, relative to the total weight of the emulsion, and further, for example, from 33% to 38% by weight, relative to the total weight of the emulsion.

The expression "volatile oil" is understood to mean an oil (or a non-aqueous medium) capable of evaporating upon contact with the skin in less than one hour, at room temperature and atmospheric pressure. The volatile oil is a volatile cosmetic oil, which is liquid at room temperature, having, for example, a non-zero vapor pressure, at room temperature and atmospheric pressure, for example, having a vapor pressure ranging, for example, from 0.13 Pa to 40 000 Pa ($10^{-3}$ to 300 mmHg), and, for example, ranging from 1.3 Pa to 13 000 Pa (0.01 to 100 mmHg), and further, for example, ranging from 1.3 Pa to 1 300 Pa (0.01 to 10 mmHg).

In addition, the at least one volatile oil generally has a boiling point, measured at atmospheric pressure, ranging, for example, from 150° C. to 260° C., and further, for example, ranging from 170° C. to 250° C.

The expression "hydrocarbon oil" is understood to mean an oil, for example, comprising carbon and hydrogen atoms, and optionally oxygen and nitrogen atoms, and comprising no silicon or fluorine atom; it may comprise at least one group chosen from ester, ether, amine and amide groups.

The expression "silicone oil" is understood to mean an oil comprising at least one silicon atom, and for example, comprising at least one Si—O group.

The expression "fluorinated oil" is understood to mean an oil comprising at least one fluorine atom.

The at least one volatile hydrocarbon oil which can be used in the composition disclosed herein may be chosen from hydrocarbon oils having a flash point ranging, for example, from 40° C. to 102° C., for example, ranging from 40° C. to 55° C., and further, for example, ranging from 40° C. to 50° C.

The at least one volatile hydrocarbon oil may be chosen, for example, from volatile hydrocarbon oils comprising from 8 to 16 carbon atoms, for example, branched $C_8$-$C_{16}$ alkanes such as $C_8$-$C_{16}$ isoalkanes (also called isoparaffins), isododecane, isodecane, isohexadecane and for example the oils sold under the trade name Isopars and Permetyls, branched $C_8$-$C_{16}$ esters such as isohexyl neopentanoate. For example, the at least one volatile hydrocarbon oil may, for example, be chosen from volatile hydrocarbon oils comprising from 8 to 16 carbon atoms, for example, isododecane, isodecane, isohexadecane, and, for example, isododecane.

The at least one volatile hydrocarbon oil may be present in an amount ranging, for example, from 6% to 25% by weight, relative to the total weight of the emulsion, for example, ranging from 10% to 20% by weight, relative to the total weight of the emulsion, and further, for example, ranging from 10% to 15% by weight, relative to the total weight of the emulsion. In another embodiment, the composition comprises at least 10% by weight, relative to the total weight of the emulsion, of at least one volatile oil.

The volatile silicone oils which can be used in the composition disclosed herein may, for example, be chosen from silicone oils having a flash point ranging from 40° C. to 102° C., for example, having a flash point greater than 55° C. and less than or equal to 95° C., and further, for example, ranging from 65° C. to 95° C.

The volatile silicone oils may, for example, be chosen from linear and cyclic silicone oils comprising from 2 to 7 silicon atoms, these silicones optionally comprising at least one group chosen from alkyl and alkoxy groups comprising from 1 to 10 carbon atoms. For example, the volatile silicone oils may be chosen from at least one of octamethylcyclotetrasiloxane, decamethylcyclopentasiloxane, dodeca-methylcyclohexasiloxane, heptamethylhexyltrisiloxane, heptamethyloctyltrisiloxane, hexamethyldisiloxane, octamethyltrisiloxane, decamethyltetrasiloxane, and dodecamethylpentasiloxane.

The volatile fluorinated oils generally have no flash point. The volatile fluorinated oils may, for example, be chosen from at least one of nonafluoroethoxybutane, nonafluoromethoxybutane, decafluoropentane, tetradecafluorohexane, and dodecafluoro-pentane.

The at least one volatile oil chosen from volatile silicone oils and volatile fluorinated oils may be present in an amount ranging, for example, from 20% to 32% by weight, relative to the total weight of the emulsion, further, for example, ranging from 20% to 30% by weight, relative to the total weight of the emulsion, and further, for example, ranging from 22% to 26% by weight, relative to the total weight of the emulsion.

For example, in one embodiment disclosed herein the volatile fatty phase of the composition comprises:

a first volatile hydrocarbon oil, a second silicone oil having a flash point ranging, for example, from greater than 55° C. to less than or equal to 85° C., for example, ranging from 65° C. to 80° C., or ranging from 67° C. to 85° C., and a third volatile silicone oil having a flash point, for example, greater than 80° C., for example, ranging from greater than 80° C. to less than or equal to 95° C., and, for example, ranging from 87° C. to 95° C.

In this embodiment:

the first volatile hydrocarbon oil may be chosen from isoparaffins, for example, isododecane;

the second volatile silicone oil may be chosen, for example, from decamethyl-cyclopentasiloxane, decamethyltetrasiloxane, and, for example, decamethylcyclopentasiloxane;

the third volatile silicone oil may, for example, be dodecamethylcyclohexasiloxane.

For example, the first volatile hydrocarbon oil, for example, isododecane, may be present in an amount ranging, for example, from 6% to 25% by weight, relative to the total weight of the emulsion, further, for example, ranging from 10% to 20% by weight, relative to the total weight of the emulsion and even further, for example, ranging from 10% to 15% by weight, relative to the total weight of the emulsion.

For example, the second volatile silicone oil, for example, decamethylcyclopentasiloxane, may be present in an amount ranging, for example, from 0.1% to 31.9% by weight, relative to the total weight of the emulsion, further, for example, ranging from 5% to 20% by weight, relative to the total weight of the emulsion, and even further, for example, ranging from 8% to 16% by weight, relative to the total weight of the emulsion.

For example, the third volatile silicone oil, for example, dodecamethylcyclohexasiloxane, may be present in an amount ranging from 0.1% to 31.9% by weight, relative to the total weight of the emulsion, further, for example, ranging from 5% to 20% by weight, relative to the total weight of the emulsion, and even further, for example, ranging from 8% to 16% by weight, relative to the total weight of the emulsion.

For example, one embodiment of the composition disclosed herein is a foundation wherein the volatile fatty phase comprises at least 30% by weight, relative to the total weight of the emulsion, of a mixture of decamethylcyclopentasiloxane, dodecamethylcyclohexasiloxane and isododecane, wherein the isododecane is present in an amount, for example, of at least 6% by weight, relative to the total weight of the emulsion, for example, of at least 10% by weight, relative to the total weight of the emulsion.

The fatty phase of the emulsion disclosed herein may additionally comprise at least one additional non-volatile oil.

The at least one additional non-volatile oil may be present in an amount ranging, for example, from 0.1% to 12% by weight, relative to the total weight of the emulsion, and further, for example, ranging from 1% to 5% by weight, relative to the total weight of the emulsion.

The emulsion, for example, comprises from 30% to 45% by weight, relative to the total weight of the emulsion, of oils, wherein said oils comprise at least one volatile hydrocarbon oil, at least one volatile oil, and at least one additional non-volatile oil, and, for example, from 30% to 40% by weight, relative to the total weight of the emulsion, of oils, wherein said oils comprise at least one volatile hydrocarbon oil, at least one volatile oil, and at least one additional non-volatile oil.

The at least one non-volatile additional oil may be chosen, for example, from carbonaceous, hydrocarbon and silicone oils of mineral, animal, plant and synthetic origin, as long as they are compatible with the envisaged use.

The at least one non-volatile hydrocarbon oil may, for example, be chosen from paraffin oil, liquid paraffin, isoeicosane, mink oil, turtle oil, soya bean oil, perhydrosqualene, sweet almond oil, calophyllum oil, palm oil, grapeseed oil, sesame oil, maize oil, arara oil, rapeseed oil, sunflower oil, cottonseed oil, apricot oil, castor oil, avocado oil, jojoba oil, olive oil, and cereal germ oil; esters of lanolic acid, oleic acid, lauric acid and stearic acid; fatty esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyidecyl palmitate, 2-octyidodecyl myristate, 2-octyldodecyl lactate, 2-diethylhexyl succinate, diisostearyl malate, glycerine triisostearate, and diglycerine triisostearate; higher fatty acids such as myristic acid, palmitic acid, stearic acid, behenic acid, oleic acid, linoleic acid, linolenic acid, and isostearic acid; higher fatty alcohols such as cetanol, stearyl alcohol, oleyl alcohol, linoleyl alcohol, linolenyl alcohol, isostearyl alcohol, and octyldodecanol.

The at least one additional non-volatile silicone oil may, for example, be chosen from polysiloxanes modified with fatty acids, fatty alcohols, and polyoxyalkylenes; and polydimethylsiloxanes (PDMS), which may be optionally phenylated, such as phenyltrimethicones, and/or which may be optionally substituted with at least one group chosen from aliphatic and aromatic groups, and/or with at least one functional group, for example, chosen from hydroxyl, thiol and amine groups.

The fatty phase may further comprise at least one fatty substance chosen from waxes, gums and pasty fatty substances, wherein the pasty fatty substances may be chosen from pasty fatty substances of plant origin, animal origin, mineral origin, synthetic origin, and even silicone-based fatty substances.

The waxes solid at room temperature, which may be present in the emulsion disclosed herein, may, for example, be chosen from at least one of hydrocarbon waxes such as beeswax, Carnauba wax, Candelilla wax, Ouricoury wax, Japan wax, cork fibre waxes, sugarcane waxes, paraffin waxes, lignite waxes, microcrystalline waxes, lanolin wax, Montan wax, ozokerites, polyethylene waxes, waxes obtained by Fischer-Tropsch synthesis, hydrogenated oils, fatty esters and glycerides which are concrete at 25° C. The waxes may also, for example, be chosen from silicone waxes, for example, silicone waxes chosen from alkyl, alkoxy and esters of polymethylsiloxane. The waxes may be provided in the form of stable dispersions of colloidal particles of wax as may be prepared according to known methods, such as those of "Microemulsions Theory and Practice", L. M. Prince Ed., Academic Press (1977), pages 21-32. A wax which is liquid at room temperature, such as jojoba oil, may also be used in the emulsions disclosed herein.

The waxes may be present in an amount ranging, for example, from 0.1% to 10% by weight, relative to the total weight of the emulsion, and further, for example, from 0.1% to 5% by weight, relative to the total weight of the emulsion.

The pasty fatty compounds may be defined by at least one of the following physicochemical properties:
  a viscosity ranging, for example, from 0.1 to 40 Pa·s (1 to 400 poises), for example, from 0.5 to 25 Pa·s, measured at 40° C. with a CONTRAVES TV rotary viscometer equipped with an MS-r3 or MS-r4 rotor at a frequency of 60 Hz, and
  a melting point ranging, for example, from 25 to 70° C., and further, for example, ranging from 25 to 55° C.

The emulsions disclosed herein may also comprise at least one of alkyl, alkoxy and phenyl dimethicones such as, for example, the product sold under the name "Abil wax 2440" by the company GOLDSCHMIDT.

The compositions disclosed herein may also comprise at least one silicone resin comprising a combination of $R_3SiO_{1/2}$, $R_2SiO_{2/2}$, $RSiO_{3/2}$ and $SiO_{4/2}$ units wherein R is chosen from alkyl radicals comprising from 1 to 6 carbon atoms.

The emulsion disclosed herein may further comprise at least one fatty phase thickening agent. The at least one fatty phase thickening agent may, for example, be chosen from:
organomodified clays which are clays treated with compounds chosen, for example, from quaternary amines and tertiary amines. The organomodified clays may, for example, be chosen from organomodified bentonites such as those sold under the name "Bentone 34" by the company RHEOX, and organomodified hectorites such as those sold under the name "Bentone 27", "Bentone 38" by the company RHEOX.
hydrophobic pyrogenic silicas, which is a pyrogenic silica which is chemically surface-modified by a chemical reaction generating a reduction in the number of silanol groups. The silanol groups may be replaced, for example, by at least one hydrophobic group.

The at least one hydrophobic group may, for example, be chosen from:
trimethylsiloxyl groups, which are obtained, for example, by treating pyrogenic silica in the presence of hexamethyldisilazane. Silicas thus treated are called "Silica silylate" according to CTFA ($6^{th}$ edition, 1995). They are, for example, marketed under the references "AEROSIL R812®" by the company Degussa, "CAB-O-SIL TS-530®" by the company Cabot.
dimethylsilyloxyl and polydimethylsiloxane groups, which are, for example, obtained by treating pyrogenic silicas in the presence of polydimethylsiloxane or dimethyldichlorosilane. Silicas thus treated are called "Silica dimethyl silylate" according to CTFA (6th edition, 1995). They are, for example, marketed under the references "AEROSIL R972®", "AEROSIL R974®" by the company Degussa, "CAB-O-SIL TS-610®", "CAB-O-SIL TS-720®" by the company Cabot.

The pyrogenic silicas may have, for example, an average particle size which may be nanometric or micrometric, for example, ranging from about 5 to 200 nm. Such an average particle size can be readily determined by one of ordinary skill in the art using known techniques.

The at least one fatty phase thickening agent may be present in an amount ranging, for example, from 0.1% to 5% by weight, relative to the total weight of the emulsion, and further, for example, from 0.4% to 3% by weight, relative to the total weight of the emulsion.

The fatty phase may be present in an amount ranging, for example, from 22% to 50% by weight, relative to the total weight of the emulsion, further, for example, from 25% to 45% by weight, relative to the total weight of the emulsion, even further, for example, from 30% to 45% by weight, relative to the total weight of the emulsion, further, for example, from 35% to 45% by weight, relative to the total weight of the emulsion. The fatty phase may also be present, for example, in an amount ranging from 30% to 40% by weight, relative to the total weight of the emulsion.

The aqueous phase comprises water. The water may be chosen from at least one of floral water such as cornflower water; mineral water such as VITTEL water, LUCAS water and LA ROCHE POSAY water; and thermal water.

The aqueous phase may also comprise at least one solvent other than water. For example, the at least one solvent may be chosen from primary alcohols such as ethanol and isopropanol; glycols such as propylene glycol, butylene glycol, dipropylene glycol, and diethylene glycol; glycol ethers such as ($C_1$-$C_4$)alkyl ether of mono-, di- and tripropylene glycol, mono-, di- and triethylene glycols.

The aqueous phase may further comprise, in addition, at least one stabilizing agent. The at least one stabilizing agent may, for example, be chosen from sodium chloride, magnesium dichloride and magnesium sulphate.

The aqueous phase may also comprise at least one entity chosen from water-soluble and water-dispersible entities compatible with an aqueous phase, such as gelling agents, film-forming polymers, thickeners, and surfactants.

For example, the aqueous phase may be present in the emulsion disclosed herein in an amount ranging from 30% to 50% by weight, relative to the total weight of the emulsion, further, for example, ranging from 35% to 45% by weight, relative to the total weight of the emulsion.

The emulsion disclosed herein may also comprise at least one filler. The expression "filler" means colorless or white, inorganic or synthetic, lamellar or non-lamellar particles.

The at least one filler may be present in the emulsion disclosed herein in an amount ranging, for example, from 0.1% to 10% by weight, relative to the total weight of the emulsion, and further, for example, ranging from 0.1% to 7% by weight, relative to the total weight of the emulsion. The at least one filler may, for example, be chosen from talc, mica, silica, kaolin, starch, boron nitride, calcium carbonate, magnesium carbonate, magnesium hydrocarbonate, microcrystalline cellulose, powders of synthetic polymers such as polyethylene, polyesters, polyamides such as those sold under the tradename "Nylon", polytetrafluoroethylene ("Teflon") and silicone powders.

For example, the emulsion disclosed herein may have a viscosity, measured at 25° C., at a shear rate of 200 $\min^{-1}$ (200 revolutions per minute, that is a frequency of 50 Hz), ranging, for example, from 0.15 to 0.6 Pa·s (15 to 6 poises), for example, ranging from 0.25 to 0.45 Pa·s (2.5 to 4.5 poises). Such a viscosity may allow easy application of the composition, and may make it possible to obtain a make-up which is homogeneous, uniform and without marks. The viscosity is measured at 25° C. with a TV type CONTRAVES viscometer equipped with a No. 2 rotor, the measurement being carried out after 10 minutes of rotation of the rotor (time after which stabilization of the viscosity and of the speed of rotation of the rotor is observed), at a shear rate of 200 $\min^{-1}$.

In a known manner, all the emulsions disclosed herein may comprise at least one adjuvant chosen from customary adjuvants used in the cosmetic and dermatological fields, such as hydrophilic and lipophilic gelling and thickening agents; moisturizing agents; emollients; hydrophilic active agents; lipophilic active agents; anti-free radical agents; sequestrants; antioxidants; preservatives; basifying agents; acidifying agents; perfumes; film-forming agents; and soluble colorants. The quantity of the at least one adjuvant is that conventionally used in foundations.

The active agents which may be used in the emulsion disclosed herein, may, for example, be chosen from at least one of moisturizing agents such as protein hydrolysates and polyols such as glycerine, glycols such as polyethylene glycols, and sugar derivatives; natural extracts; anti-inflammatory agents; procyannidolic oligomers; vitamins such as vitamin A (retinol), vitamin E (tocopherol), vitamin C (ascorbic acid), vitamin B5 (panthenol), vitamin B3 (niacinamide), and derivatives thereof, for example esters; urea; caffeine; salicylic acid and derivatives thereof; alpha-hydroxy acids such as lactic acid and glycolic acid and derivatives thereof; retinoids such as carotenoids and derivatives of vitamin A; sunscreens; hydrocortisone; melatonin; extracts of algae, fungi, plants, yeasts and bacteria; enzymes; steroids; anti-bacterial active agents such as 2,4,4'-trichloro-2'-hydroxydiphenyl ether (or triclosan), 3,4,4'-trichlorocarbanilide (or triclocarban) and the acids indicated above, for example, salicylic acid and derivatives thereof; and tightening agents.

The sunscreens (or UV-screening agents) may be chosen from at least one of organic screening agents (or chemical sunscreens), and physical screening agents.

The organic screening agents (or chemical sunscreens) which may be used in the emulsion disclosed herein may be chosen, for example, from any UVA- and UVB-screening agents which may be used in the cosmetic field.

The UVB-screening agents may, for example, be chosen from at least one of:
(1) salicylic acid derivatives, for example, homomenthyl salicylate and octyl salicylate;
(2) cinnamic acid derivatives, for example, 2-ethylhexyl p-methoxycinnamate, marketed by the company Givaudan under the name Parsol MCX;
(3) liquid β,β'-diphenylacrylate derivatives, for example, 2-ethylhexyl α-cyano-α,β-diphenylacrylate and octocrylene, marketed by the company BASF under the name UVINUL N539;
(4) p-aminobenzoic acid derivatives;
(5) 4-methylbenzylidenecamphor marketed by the company Merck under the name EUSOLEX 6300;
(6) 2-phenylbenzimidazole-5-sulphonic acid marketed under the name EUSOLEX 232 by the company Merck; and
(7) 1,3,5-triazine derivatives, for example:

2,4,6-tris[p-(2'-ethylhexyl-1'-oxycarbonyl)anilino]-1,3,5-triazine marketed by the company BASF under the name UVINUL T150, and dioctylbutamidotriazone marketed by the company Sigma 3V under the name UVASORB HEB.

The UVA-screening agents may, for example, be chosen from at least one of:
(1) dibenzoylmethane derivatives, for example, 4-(tert-butyl)-4'-methoxydibenzoylmethane marketed by the company Givaudan under the name PARSOL 1789;
(2) 1,4-benzene[di(3-methylidene-10-camphorsulphonic)] acid optionally in partially and completely neutralized form, marketed under the name MEXORYL SX by the company Chimex;
(3) benzophenone derivatives, for example:

2,4-dihydroxybenzophenone (benzophenone-1);

2,2',4,4'-tetrahydroxybenzophenone (benzophenone-2);

2-hydroxy-4-methoxybenzophenone (benzophenone-3), marketed under the name UVINUL M40 by the company BASF;

2-hydroxy-4-methoxybenzophenone-5-sulphonic acid (benzophenone-4) and its sulphonate form (benzophenone-5), marketed by the company BASF under the name UVINUL MS40;

2,2'-dihydroxy-4,4'-dimethoxybenzophenone (benzophenone-6);

5-chloro-2-hydroxybenzophenone (benzophenone-7);

2,2'-dihydroxy-4-methoxybenzophenone (benzophenone-8);

the disodium salt of 2,2'-dihydroxy-4,4'-dimethoxybenzophenone-5,5'-disulphonic diacid (benzophenone-9);

2-hydroxy-4-methoxy-4'-methylbenzophenone (benzophenone-10); benzophenone-11;

2-hydroxy-4-(octyloxy)benzophenone (benzophenone-12);
(4) silane derivatives and polyorganosiloxanes comprising at least one benzophenone group;
(5) anthranilates, for example, menthyl anthranilate marketed by the company Haarman & Reiner under the name NEO HELIOPAN MA;
(6) compounds comprising, per molecule, at least two benzoazolyl groups or at least one benzodiazolyl group, for example, 1,4-bis-benzimidazolyl-phenylene-3,3', 5,5'-tetrasulphonic acid, and salts thereof, marketed by the company Haarman & Reimer;
(7) silicon-containing derivatives of N-substituted benzimidazolyl-benzazoles and of benzofuranyl-benzazoles, for example:

2-[1-[3-[1,3,3,3-tetramethyl-1-[(trimethylsilyl)oxy]disiloxanyl]propyl]-1H-benzimidazol-2-yl]benzoxazole;

2-[1-[3-[1,3,3,3-tetramethyl-1-[(trimethylsilyl)oxy]disiloxanyl]propyl]-1H-benzimidazol-2-yl]benzothiazole;

2-[1-(3-trimethylsilanylpropyl)-1H-benzimidazol-2-yl]benzoxazole;

6-methoxy-1,1'-bis(3-trimethylsilanylpropyl)-1H,1'H-[2,2'] dibenzimidazolylbenzoxazole;

2-[1-(3-trimethylsilanylpropyl)-1H-benzimidazol-2-yl]benzothiazole; which are described in patent application EP-A-1 028 120;
(8) triazine derivatives, for example, 2,4-bis{[4-(2-ethylhexyloxy]-2-hydroxylphenyl}-6-(4-methoxyphenyl)-1,3,5-triazine marketed by the company Ciba Geigy under the name TINOSORB S, and 2,2'-methylenebis-[6-(2H-benzotriazol-2-yl)-4-(1,1,3,3-tetramethylbutyl)-phenol] marketed by the company Ciba Geigy under the name TINOSORB M.

It is also possible to use a mixture of several of these screening agents and a mixture of UVB-screening agents and UVA-screening agents and also mixtures with physical screening agents.

The physical screening agents may, for example, be chosen from at least one of titanium oxide (amorphous and crystalline titanium dioxide in rutile and anatase form), zinc oxide, iron oxide, zirconium oxide or cerium oxide. These metal oxides may, for example, be in the form of particles having a micrometer or nanometer size (nanopigments). In the form of nanopigments, the average sizes of the particles can range, for example, from 5 to 100 nm. Such an average particle size can be readily determined by one of ordinary skill in the art using known techniques.

These pigments may, for example, be treated so as to make their surface hydrophobic. This treatment may be carried out according to methods known to persons skilled in the art; the pigments may, for example, be coated with silicone compounds such as PDMS and/or with polymers.

Of course, persons skilled in the art will be careful to choose the possible adjuvant(s) added to the emulsion disclosed herein such that the advantageous properties intrinsically attached to the emulsion disclosed herein are not, or not substantially, impaired by the addition envisaged.

The embodiments disclosed herein are illustrated in greater detail in the following examples.

EXAMPLE 1

A foundation was prepared in the form of a water-in-oil emulsion having the following composition:

| Oily phase: | |
|---|---|
| Isododecane | 13 g |
| Cyclopentasiloxane | 16 g |
| Cyclohexasiloxane | 8 g |
| Polydimethylsiloxane (DC 200 Fluid - 5 cst from the company DOW CORNING) | 2 g |
| Isoeicosane | 3 g |
| Cetyl dimethicone copolyol (Abil ® Em 90 from the company GOLDSCHMIDT) | 0.8 g |
| Dimethicone copolyol (KF6017 from Shin Etsu) | 5 g |
| Polyglyceryl isostearate (4 mol of glycerol) | 0.6 g |
| Hectorite | 1.4 g |
| Iron oxides coated with perfluoroalkyl phosphate | 2 g |
| Titanium oxide coated with perfluoroalkyl phosphate | 5.5 g |
| Nylon powder | 4 g |

| Aqueous phase: | |
|---|---|
| Butylene glycol | 10 g |
| Sodium chloride | 0.7 g |
| Preservatives | |
| Water qs | 100 g |

The emulsion was prepared at room temperature, on the one hand, by mixing the pigments in part of the cyclopentasiloxane, on the other hand, by mixing the other oils with the surfactants, and then the mixture of pigments and the nylon was added to the other mixed constituents of the fatty phase. The mixture of the constituents of the aqueous phase was then prepared and poured into the mixture of the fatty phase, with stirring, according to known means in order to finally obtain the emulsion.

This foundation was stable after storing at room temperature (25° C.) for 4 months. It was easy to apply to the skin with a good sensation of unctuousness and of softness, a very good slipperiness; it dried rapidly after application of the product, and the make-up obtained exhibited good color homogeneity, without leaving any mark on the skin.

EXAMPLE 2

A foundation was prepared in the form of a water-in-oil emulsion having the following composition:

| Oily Phase: | |
| --- | --- |
| Isododecane | 13 g |
| Cyclopentasiloxane | 16 g |
| Cyclohexasiloxane | 6.8 g |
| Polydimethylsiloxane (DC 200 Fluid - 5 cst from the company DOW CORNING) | 2 g |
| Isoeicosane | 3 g |
| Cetyl dimethicone copolyol (Abil ® Em 90 from the company GOLDSCHMIDT) | 2 g |
| Dimethicone copolyol (KF6017 from Shin Etsu) | 5 g |
| Polyglyceryl isostearate (4 mol of glycerol) | 0.6 g |
| Hectorite | 1.4 g |
| Iron oxides coated with perfluoroalkyl phosphate | 2 g |
| Titanium oxide coated with perfluoroalkyl phosphate | 5.5 g |
| Nylon powder | 4 g |

| Aqueous phase: | |
| --- | --- |
| Butylene glycol | 10 g |
| Sodium chloride | 0.7 g |
| Preservatives | |
| Water qs | 100 g |

The foundation exhibited good stability at room temperature. It was easy to apply to the skin with no sensation of greasiness; it dried rapidly after application of the product to the skin; the make-up obtained exhibited good color homogeneity, without leaving any mark on the skin.

What is claimed is:

1. A foundation in the form of a water-in-oil emulsion comprising:
   a fatty phase;
   an aqueous phase;
   at least one surfactant chosen from $C_8$-$C_{22}$ alkyl dimethicone copolyols;
   at least one other surfactant chosen from dimethicone copolyols, wherein the at least one other surfactant chosen from dimethicone copolyols is present in an amount ranging from 5% to 10% by weight, relative to the total weight of the emulsion; and
   hydrophobic coated pigments,
wherein the fatty phase comprises at least 30% by weight, relative to the total weight of the emulsion, of a volatile fatty phase comprising:
   at least 6% by weight, relative to the total weight of the emulsion, of at least one volatile hydrocarbon oil; and
   at least one volatile oil chosen from volatile silicone oils and volatile fluorinated oils.

2. The foundation according to claim 1, wherein the dimethicone copolyols are chosen from compounds of the following formula (IV):

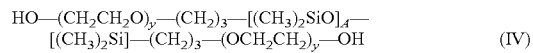

(IV)

wherein:
   A' and y, which may be identical or different, are each an integer ranging from 10 to 20.

3. The foundation according to claim 1, wherein the at least one other surfactant chosen from dimethicone copolyols is present in an amount ranging from 5% to 8% by weight, relative to the total weight of the emulsion.

4. The foundation according to claim 3, wherein the at least one other surfactant chosen from dimethicone copolyols is present in an amount ranging from 5% to 7% by weight, relative to the total weight of the emulsion.

5. The foundation according to claim 1, wherein the hydrophobic coated pigments are chosen from pigments treated with at least one hydrophobic agent.

6. The foundation according to claim 5, wherein the pigments are chosen from at least one of metal oxides, manganese violet, ultramarine blue, Prussian blue, ferric blue, bismuth oxychloride, pearl, mica coated with titanium, mica coated with bismuth oxychloride, and colored pearlescent pigments.

7. The foundation according to claim 6, wherein the metal oxides are chosen from at least one of iron oxides and titanium dioxides.

8. The foundation according to 5, wherein the at least one hydrophobic agent is chosen from silicones, fatty acids, metal soaps, perfluoroalkyl phosphates, perfluoroalkylsilanes, perfluoroalkylsilazanes, polyhexafluoropropylene oxides, polyorganosiloxanes comprising at least one perfluoroalkyl perfluoropolyether group, amino acids, N-acylated amino acids and salts thereof, lecithin, and isopropyl triisostearyl titanate.

9. The foundation according to claim 8, wherein the N-acylated amino acids comprise at least one acyl group comprising from 8 to 22 carbon atoms.

10. The foundation according to claim 1, wherein the hydrophobic coated pigments are present in an amount ranging from 0.5% to 20% by weight, relative to the total weight of the emulsion.

11. The foundation according to claim 10, wherein the hydrophobic coated pigments are present in an amount ranging from 5% to 20% by weight, relative to the total weight of the emulsion.

12. The foundation according to claim 11, wherein the hydrophobic coated pigments are present in an amount ranging from 8% to 20% by weight, relative to the total weight of the emulsion.

13. The foundation according to claim 12, wherein the hydrophobic coated pigments are present in an amount ranging from 8% to 15% by weight, relative to the total weight of the emulsion.

14. The foundation according to claim 1, wherein the volatile fatty phase is present in an amount ranging from 30% to 45% by weight, relative to the total weight of the emulsion.

15. The foundation according to claim 14, wherein the volatile fatty phase is present in an amount ranging from 30% to 40% by weight, relative to the total weight of the emulsion.

16. The foundation according to claim 15, wherein the volatile fatty phase is present in an amount ranging from 33% to 38% by weight, relative to the total weight of the emulsion.

17. The foundation according to claim 1, wherein the at least one volatile hydrocarbon oil is chosen from hydrocarbon oils having a flash point ranging from 40° C. to 102° C.

18. The foundation according to claim 17, wherein the at least one volatile hydrocarbon oil is chosen from hydrocarbon oils having a flash point ranging from 40° C. to 55° C.

19. The foundation according to claim 18, wherein the at least one volatile hydrocarbon oil is chosen from hydrocarbon oils having a flash point ranging from 40° C. to 50° C.

20. The foundation according to claim 1, wherein the at least one volatile hydrocarbon oil is chosen from volatile hydrocarbon oils comprising from 8 to 16 carbon atoms.

21. The foundation according to claim 1, wherein the at least one volatile hydrocarbon oil is chosen from branched $C_8$-$C_{16}$ alkanes and branched $C_8$-$C_{16}$ esters.

22. The foundation according to claim 1, wherein the at least one volatile hydrocarbon oil is chosen from isododecane, isodecane and isohexadecane.

23. The foundation according to claim 1, wherein the at least one volatile hydrocarbon oil is isododecane.

24. The foundation according to claim 1, wherein the at least one volatile hydrocarbon oil is present in an amount ranging from 6% to 25% by weight, relative to the total weight of the emulsion.

25. The foundation according to claim 24, wherein the at least one volatile hydrocarbon oil is present in an amount ranging from 10% to 20% by weight, relative to the total weight of the emulsion.

26. The foundation according to claim 25, wherein the at least one volatile hydrocarbon oil is present in an amount ranging from 10% to 15% by weight, relative to the total weight of the emulsion.

27. The foundation according to claim 1, wherein the volatile silicone oils are chosen from silicone oils having a flash point ranging from 40° C. to 102° C.

28. The foundation according to claim 27, wherein the volatile silicone oils are chosen from silicone oils having a flash point ranging from greater than 55° C. to less than or equal to 95° C.

29. The foundation according to claim 28, wherein the volatile silicone oils are chosen from silicone oils having a flash point ranging from 65° C. to 95° C.

30. The foundation according to claim 1, wherein the volatile silicone oils are chosen from linear and cyclic silicone oils comprising from 2 to 7 silicon atoms, these silicones optionally comprising at least one group chosen from alkyl and alkoxy groups comprising from 1 to 10 carbon atoms.

31. The foundation according to claim 1, wherein the volatile silicone oils are chosen from at least one of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, and dodecamethylpentasiloxane.

32. The foundation according to claim 1, wherein the volatile fluorinated oils are chosen from at least one of nonafluoroethoxybutane, nonafluoromethoxybutane, decafluoropentane, tetradecafluorohexane, and dodecafluoropentane.

33. The foundation according to claim 1, wherein the volatile fatty phase comprises at least one volatile hydrocarbon oil and at least one volatile silicone oil.

34. The foundation according to claim 1, wherein the at least one volatile oil chosen from volatile silicone oils and volatile fluorinated oils is present in an amount ranging from 20% to 32% by weight, relative to the total weight of the emulsion.

35. The foundation according to claim 34, wherein the at least one volatile oil chosen from volatile silicone oils and volatile fluorinated oils is present in an amount ranging from 20% to 30% by weight, relative to the total weight of the emulsion.

36. The foundation according to claim 35, wherein the at least one volatile oil chosen from volatile silicone oils and volatile fluorinated oils is present in an amount ranging from 22% to 26% by weight, relative to the total weight of the emulsion.

37. The foundation according to claim 1, wherein the volatile fatty phase comprises:
a first volatile hydrocarbon oil,
a second volatile silicone oil having a flash point ranging from greater than 55° C. to less than or equal to 85° C.,
a third volatile silicone oil having a flash point greater than 80° C.

38. The foundation according to claim 37, wherein the flashpoint of the second volatile silicone oil ranges from 65° C. to 80° C.

39. The foundation according to claim 37, wherein the flashpoint of the second volatile silicone oil ranges from 67° C. to 85° C.

40. The foundation according to claim 37, wherein the flashpoint of the third volatile silicone oil ranges from greater than 80° C. to less than or equal to 95° C.

41. The foundation according to claim 37, wherein the flashpoint of the third volatile silicone oil ranges from 87° C. to 95° C.

42. The foundation according to claim 37, wherein the first volatile hydrocarbon oil is isododecane.

43. The foundation according to claim 37, wherein the second volatile oil is chosen from decamethylcyclopentasiloxane and decamethyltetrasiloxane.

44. The foundation according to claim 37, wherein the second volatile silicone oil is decamethylcyclopentasiloxane.

45. The foundation according to claim 37, wherein the third volatile silicone oil is dodecamethylcyclohexasiloxane.

46. The foundation according to claim 37, wherein the second volatile silicone oil is present in an amount ranging from 0.1% to 31.9% by weight, relative to the total weight of the emulsion.

47. The foundation according to claim 46, wherein the second volatile silicone oil is present in an amount ranging from 5% to 20% by weight, relative to the total weight of the emulsion.

48. The foundation according to claim 47, wherein the second volatile silicone oil is present in an amount ranging from 8% to 16% by weight, relative to the total weight of the emulsion.

49. The foundation according to claim 37, wherein the third volatile silicone oil is present in an amount ranging from 0.1% to 31.9% by weight, relative to the total weight of the emulsion.

50. The foundation according to claim 49, wherein the third volatile silicone oil is present in an amount ranging from 5% to 20% by weight, relative to the total weight of the emulsion.

51. The foundation according to claim 1, wherein the volatile fatty phase comprises at least 30% by weight, relative to the total weight of the emulsion, of a mixture of decamethylcyclopentasiloxane, dodecamethylcyclohexasiloxane and isododecane, wherein the isododecane content is at least 6% by weight, relative to the total weight of the emulsion.

52. The foundation according to claim 51, wherein the third volatile silicone oil is present in an amount ranging from 8% to 16% by weight, relative to the total weight of the emulsion.

53. The foundation according to claim 51, wherein the isododecane content is at least 10% by weight, relative to the total weight of the emulsion.

54. The foundation according to claim 1, further comprising at least one non-volatile additional oil.

55. The foundation according to claim 54, wherein the at least one non-volatile additional oil is chosen from non-volatile hydrocarbon oils and non-volatile silicone oils.

56. The foundation according to claim 54, wherein the at least one non-volatile additional oil is present in an amount ranging from 0.1% to 12% by weight, relative to the total weight of the emulsion.

57. The foundation according to claim 56, wherein the at least one non-volatile additional oil is present in an amount ranging from 1% to 5% by weight, relative to the total weight of the emulsion.

58. The foundation according to claim 54, wherein the emulsion comprises from 30% to 45% by weight of oils, relative to the total weight of the emulsion, wherein said oils comprise at least one volatile hydrocarbon oil, at least one volatile oil, and at least one additional non-volatile oil.

59. The foundation according to claim 58, wherein the emulsion comprises from 30% to 40% by weight of oils, relative to the total weight of the emulsion, wherein said oils comprise at least one volatile hydrocarbon oil, at least one volatile oil, and at least one additional non-volatile oil.

60. The foundation according to claim 1, further comprising at least one fatty substance chosen from waxes, gums, and pasty fatty substances.

61. The foundation according to claim 1, further comprising at least one fatty phase thickening agent.

62. The foundation according to claim 61, wherein the at least one fatty phase thickening agent is chosen from organo-modified clays and hydrophobic pyrogenic silicas.

63. The foundation according to claim 62, wherein the at least one fatty phase thickening agent is present in an amount ranging from 0.1% to 5% by weight, relative to the total weight of the emulsion.

64. The foundation according to claim 63, wherein the at least one fatty phase thickening agent is present in an amount ranging from 0.4% to 3% by weight, relative to the total weight of the emulsion.

65. The foundation according to claim 1, wherein the fatty phase is present in an amount ranging from 22% to 50% by weight, relative to the total weight of the emulsion.

66. The foundation according to claim 65, wherein the fatty phase is present in an amount ranging from 25% to 45% by weight, relative to the total weight of the emulsion.

67. The foundation according to claim 66, wherein the fatty phase is present in an amount ranging from 30% to 45% by weight, relative to the total weight of the emulsion.

68. The foundation according to claim 67, wherein the fatty phase is present in an amount ranging from 35% to 45% by weight, relative to the total weight of the emulsion.

69. The foundation according to claim 65, wherein the fatty phase is present in an amount ranging from 30% to 40% by weight, relative to the total weight of the emulsion.

70. The foundation according to claim 1, wherein the aqueous phase is present in an amount ranging from 30% to 50% by weight, relative to the total weight of the emulsion.

71. The foundation according to claim 70, wherein the aqueous phase is present in an amount ranging from 35% to 45% by weight, relative to the total weight of the emulsion.

72. The foundation according to claim 1, wherein the aqueous phase comprises at least one of water, at least one solvent chosen from primary alcohols, glycols, and glycol ethers, and at least one stabilizing agent.

73. The foundation according to claim 1, further comprising at least one filler.

74. The foundation according to claim 73, wherein the at least one filler is chosen from talc, mica, silica, kaolin, starch, boron nitride, calcium carbonate, magnesium carbonate, magnesium hydrocarbonate, microcrystalline cellulose, polyethylene powders, polyesters, polyamides, polytetrafluoroethylene, and silicone powders.

75. The foundation according to claim 73, wherein the at least one filler is present in an amount ranging from 0.1% to 10% by weight, relative to the total weight of the emulsion.

76. The foundation according to claim 75, wherein the at least one filler is present in an amount ranging from 0.1% to 7% by weight, relative to the total weight of the emulsion.

77. The foundation according to claim 1, further comprising at least one adjuvant chosen from gelling agents, hydrophilic thickening agents, lipophilic thickening agents, moisturizing agents; emollients; hydrophilic active agents, lipophilic active agents; anti-free radical agents; sequestrants; antioxidants; preservatives; basifying agents, acidifying agents; perfumes; film-forming agents; and soluble colorants.

78. The foundation according to claim 1, wherein the foundation has a viscosity, measured at 25° C., at a shear rate of 200 min$^{-1}$, ranging from 0.15 to 0.6 Pa·s.

79. The foundation according to claim 78, wherein the foundation has a viscosity, measured at 25° C., at a shear rate of 200 min$^{-1}$ ranging from 0.25 to 0.45 Pa·s.

80. A cosmetic process for the non-therapeutic application of make-up to the skin comprising applying to the skin a foundation composition in the form of a water-in-oil emulsion comprising:
a fatty phase;
an aqueous phase;
at least one surfactant chosen from $C_8$-$C_{22}$ alkyl dimethicone copolyols;
at least one other surfactant chosen from dimethicone copolyols, wherein the at least one other surfactant chosen from dimethicone copolyols is present in an amount ranging from 5% to 10% by weight, relative to the total weight of the emulsion; and
hydrophobic coated pigments,
wherein the fatty phase comprises at least 30% by weight, relative to the total weight of the emulsion, of a volatile fatty phase comprising:
at least 6% by weight, relative to the total weight of the emulsion, of at least one volatile hydrocarbon oil; and
at least one volatile oil chosen from volatile silicone oils and volatile fluorinated oils.

81. A process for obtaining a homogeneous make-up on the skin, comprising applying to said skin a foundation composition in the form of a water-in-oil emulsion comprising:
a fatty phase;
an aqueous phase;
at least one surfactant chosen from $C_8$-$C_{22}$ alkyl dimethicone copolyols;
at least one other surfactant chosen from dimethicone copolyols, wherein the at least one other surfactant chosen from dimethicone copolyols is present in an amount ranging from 5% to 10% by weight, relative to the total weight of the emulsion; and
hydrophobic coated pigments,
wherein the fatty phase comprises at least 30% by weight, relative to the total weight of the emulsion, of a volatile fatty phase comprising:
at least 6% by weight, relative to the total weight of the emulsion, of at least one volatile hydrocarbon oil; and
at least one volatile oil chosen from volatile silicone oils and volatile fluorinated oils.

82. A process for making a foundation composition, comprising including at least one surfactant chosen from $C_8$-$C_{22}$ alkyl dimethicone copolyols and at least one other surfactant chosen from dimethicone copolyols, wherein the at least one other surfactant chosen from dimethicone copolyols is present in an amount ranging from 5% to 10% by weight, relative to the total weight of the emulsion, in the foundation composition in the form of a water-in-oil emulsion comprising a fatty phase, an aqueous phase, and hydrophobic coated pigments, wherein the fatty phase comprises at least 30% by weight, relative to the total weight of the emulsion, of volatile fatty phase comprising:
- at least 6% by weight, relative to the total weight of the emulsion, of at least one volatile hydrocarbon oil, and
- at least one volatile oil chosen from volatile silicone oils and volatile fluorinated oils, wherein the composition has at least one property of being stable, homogeneous, and capable of obtaining a homogeneous make-up on the skin.

83. A foundation composition in the form of a water-in-oil emulsion comprising:
- a fatty phase;
- an aqueous phase;
- at least one surfactant chosen from $C_8$-$C_{22}$ alkyl dimethicone copolyols;
- at least one other surfactant chosen from dimethicone copolyols, wherein the at least one other surfactant chosen from dimethicone copolyols is present in an amount ranging from 5% to 10% by weight, relative to the total weight of the emulsion; and
- hydrophobic coated pigments, wherein the fatty phase comprises at least 30% by weight, relative to the total weight of the emulsion, of a volatile fatty phase comprising:
- at least 6% by weight, relative to the total weight of the emulsion, of at least one volatile hydrocarbon oil; and
- at least one volatile oil chosen from volatile silicone oils and volatile fluorinated oils,
- wherein the composition has at least one property of being stable, homogeneous, and capable of obtaining a homogeneous make-up on the skin.

* * * * *